(12) United States Patent
Mittermeyer

(10) Patent No.: US 7,972,305 B2
(45) Date of Patent: Jul. 5, 2011

(54) DRUG SUPPLY SYSTEM FOR CED (CONVECTION-ENHANCED DELIVERY) CATHETER INFUSIONS

(75) Inventor: Stephan Mittermeyer, Landshut (DE)

(73) Assignee: Brainlab AG, Feldkirchen (DE)

( * ) Notice: Subject to any disclaimer, the term of this patent is extended or adjusted under 35 U.S.C. 154(b) by 244 days.

(21) Appl. No.: 12/270,877

(22) Filed: Nov. 14, 2008

(65) Prior Publication Data

US 2009/0124976 A1    May 14, 2009

Related U.S. Application Data

(60) Provisional application No. 60/990,175, filed on Nov. 26, 2007.

(30) Foreign Application Priority Data

Nov. 14, 2007  (EP) .................................... 07120689

(51) Int. Cl.
*A61M 37/00*  (2006.01)
(52) U.S. Cl. .......................... 604/132; 604/133; 604/146
(58) Field of Classification Search .................. 604/181, 604/185, 131, 132, 133, 141, 142, 146
See application file for complete search history.

(56) References Cited

U.S. PATENT DOCUMENTS

| 5,080,652 | A | * | 1/1992 | Sancoff et al. | ................ | 604/132 |
| 5,399,166 | A | * | 3/1995 | Laing | ............................ | 604/146 |
| 2006/0200083 | A1 | * | 9/2006 | Freyman et al. | .............. | 604/181 |

FOREIGN PATENT DOCUMENTS

| WO | 95/15191 | 6/1995 |
| WO | 2004/093945 | 11/2004 |
| WO | 2006/096286 | 9/2006 |
| WO | 2007/062068 | 5/2007 |

* cited by examiner

*Primary Examiner* — Nicholas D Lucchesi
*Assistant Examiner* — Laura A Bouchelle
(74) *Attorney, Agent, or Firm* — Renner, Otto, Boisselle & Sklar, LLP

(57) ABSTRACT

A drug supply system for CED (convection-enhanced delivery) catheter infusions is provided, the system including a drug conducting system having a drug depot and a catheter supply line and a conveying device that provides for conveying the drug from the drug depot into the catheter supply line. The drug conducting system is a system that is closed to the outside in a fluidic seal The drug supply system further includes a conveying fluid conveying system arranged between the conveying device and the drug supply system and is connected to the conveying device and to the drug depot, via a drug displacement element, without fluid-drug contact.

15 Claims, 4 Drawing Sheets

DRUG SUPPLY SYSTEM FOR CED (CONVECTION-ENHANCED DELIVERY) CATHETER INFUSIONS

RELATED APPLICATION DATA

This application claims the priority of U.S. Provisional Application No. 60/990,175, filed on Nov. 26, 2007, which is hereby incorporated in its entirety by reference.

FIELD OF THE INVENTION

The invention relates to a drug supply system for CED (convection-enhanced delivery) catheter infusions.

BACKGROUND OF THE INVENTION

Administering drugs within the framework of "convection-enhanced delivery" (CED) is a neurosurgical application in which a catheter has to be inserted into solid brain tissue. A drug is administered very slowly through the catheter into the brain tissue. A syringe is provided for conveying the drug, wherein this term is to be understood here to very generally mean any devices which output a drug (for example, using a piston) from a depot. The syringe comprises a piston advancing device or pump device or is connected to such a device. Using this device, a certain amount of drug per time segment is mechanically and preferably automatically injected into a catheter supply line, and in most cases, this sets a constant flow rate over a number of days.

Conventional CED drug supply systems thus comprise a direct drug line from the syringe to the catheter; the conveying pressure is transferred directly onto the drug by the conveying device (syringe).

The problem with these conventional supply systems is that the drug fluid system has to be opened if the supply is to be manipulated. However, manipulations are sometimes necessary, for example if a new, refilled syringe is to be connected, or if the patient has to be separated from the supply system, in order for example to undergo a CT or MR scan. Opening the drug fluid system can cause contamination or allow air to enter the drug lines.

SUMMARY OF THE INVENTION

It is the object of the present invention to provide a drug supply system for CED catheter infusions which solves the aforesaid problems. In particular, the intention is to make the handling of the drug supply system during necessary manipulations easier and more secure.

This object is solved by a drug supply system for CED (convection-enhanced delivery) catheter infusions, comprising: a drug conducting system which comprises a drug depot and a catheter supply line; and a conveying device which provides for conveying the drug from the drug depot into the catheter supply line; wherein the drug conducting system is a system which is closed to the outside in a fluidic seal, and wherein a conveying fluid conveying system is arranged between the conveying device and the drug supply system and is connected on the one hand to the conveying device and on the other to the drug depot, via a drug displacement element, without fluid-drug contact. The sub-claims define preferred embodiments of the invention.

In common with the prior art described above, the drug supply system in accordance with the present invention comprises a drug conducting system which comprises a drug depot and a catheter supply line, as well as a conveying device which provides for conveying the drug from the drug depot into the catheter supply line. In order to solve the aforementioned problems, the present invention provides for the drug conducting system to be a system which is closed to the outside in a fluidic seal, and for a conveying fluid conveying system to be arranged between the conveying device and the drug supply system and to be connected on the one hand to the conveying device and on the other to the drug depot, via a drug displacement element, without fluid-drug contact.

In other words, an additional system is interposed as a "transport system" between the conveying device and the actual drug conduit in accordance with the present invention. If manipulations are then necessary, they can be performed at the "transport system", i.e. at the conveying fluid conveying system, without having to manipulate the drug system which is closed to the outside in a fluidic seal. If, for example, it is necessary to separate the conveying device (syringe device) from the system, in order to be able to move the patient, it can thus be separated—and subsequently reconnected in the conveying system—without having to worry about contaminating the drug system.

During a CED infusion, which can extend over a number of days, it can also be necessary—for various other reasons—to separate the syringe device from the infusion line. One of these reasons is for example that of replacing an empty drug depot with a new, filled depot; however, such a manipulation can also be necessary due to the risk of infection, and for reasons of the drug stability which is to be ensured. In order to be able to separate the conveying device (syringe or pump) from the system without risk, the drug depot which comprises the drug is provided in accordance with the invention. In order to be able to output the drug from the depot, another fluid is pumped into the drug depot, wherein the two fluids are prevented from mixing. To this end, the drug displacement element is provided.

In one embodiment of the present invention, the drug displacement element comprises a flexible, in particular elastic membrane which is arranged in or on the drug depot and, when dilated, displaces the drug from the depot into the drug conducting system, wherein the membrane can be inflatable like a balloon and can be arranged in the drug depot.

In accordance with another embodiment, the drug displacement element comprises a shifting wall in or on the drug depot, which is shifted by contact pressure from the conveying fluid and thus displaces the drug from the depot into the drug conducting system.

The conveying fluid conveying system can comprise a line system which comprises a separating and connecting point, in particular a quick-release connection. This enables easy separation and quick reconnection in the conveying system.

It is also possible, in a conveying fluid conveying system comprising a line system, to accommodate a number of auxiliary devices such as for example a three-way distributor, in particular comprising a three-way stop cock and/or straight-way cock, and/or a reflux valve.

In one embodiment variant, the drug supply system in accordance with the invention comprises a drug depot which is sub-divided into a number of chambers or comprises a number of drug depots, wherein each chamber and/or depot has a conveying fluid supply line of its own, wherein the conveying fluid supply lines can be switched individually or together and charged with conveying fluid by the conveying fluid conveying device.

As already briefly mentioned above, the conveying fluid conveying device can be a mechanically charged syringe; however, it is also possible to use any other pump or pump-like device.

In a further embodiment, a drug supply controller and/or regulator is provided for the drug supply system in accordance with the invention, which controls and/or regulates how the drug is administered. This controller and/or regulator can in particular operate in accordance with measured external parameters such as elapsed time, temperature or particular concentrations of chemical elements and/or compounds. In order to obtain such measurement data, the appropriate measurement instruments would in this case be attached to appropriately provided points, and the controlling and/or regulating device is connected to the drive of the supply system and/or conveying device.

BRIEF DESCRIPTION OF THE DRAWINGS

The invention is illustrated below in more detail on the basis of embodiments. It can comprise any of the features described here, individually or in any expedient combination. The enclosed drawings show.

DETAILED DESCRIPTION

Figure 1:
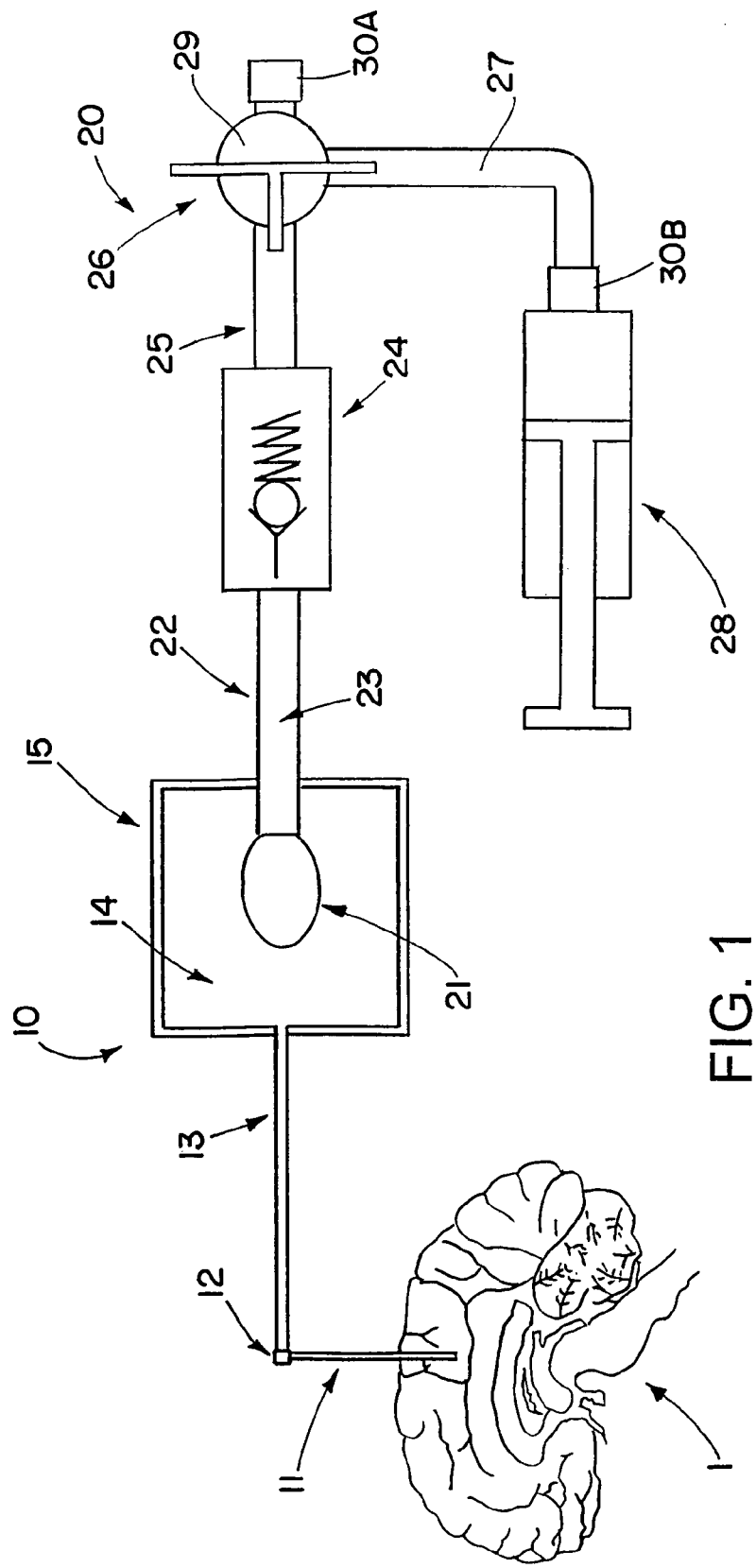
FIG. 1 a drug supply system in accordance with the invention, in accordance with a first embodiment.

The embodiment of a drug supply system in accordance with the invention as shown in FIG. 1 shows said system in its functional environment. The system serves to introduce a drug, via a catheter 11, into the solid tissue of the brain 1 shown on the left. To this end, the catheter 11 is connected at the connecting point 12 to a drug line 13 coming from the drug depot 15 and channels the drug 14 to the connecting point 12 and into the catheter 11. The part of the system from the catheter 11 to the depot 15, in which only the drug flows, is also referred to as the drug conducting system 10. The other part of the system, i.e. the conveying fluid conveying system 20, is situated between the syringe 28 and the drug depot 15 and comprises the line 27, the three-way stop cock 26 in the three-way distributor 29, the line 25, the reflux valve 24, the line 22 and the displacement body 21 which is accommodated in the depot 15. The conveying fluid 23, for example a saline solution, is accommodated in the conveying fluid conveying system 20. Quick-release connections are indicated by 30A and 30B.

If the syringe 28 then has to be changed, the three-way stop cock 26 is closed, and the syringe can be removed without losing a pressure in the system. Connecting a pre-filled syringe to a pre-filled system is often associated with pressure spikes and introducing air bubbles into the line. However, since the conveying fluid system is not directly connected to the drug system in the present case, the air is not transferred to the drug system and also cannot penetrate into the brain through the catheter. This avoids the problem of backflow at the tip of the catheter and an unpredictable distribution of the drug. While the infusion is being performed, the conveying fluid 23 flows into the displacement body 21, which in this case is constructed like a balloon from a flexible material. The displacement body will expand and move the drug 14 out of the depot 15, through the line 13, into the catheter 11 and therefore into the brain.

Figure 2:
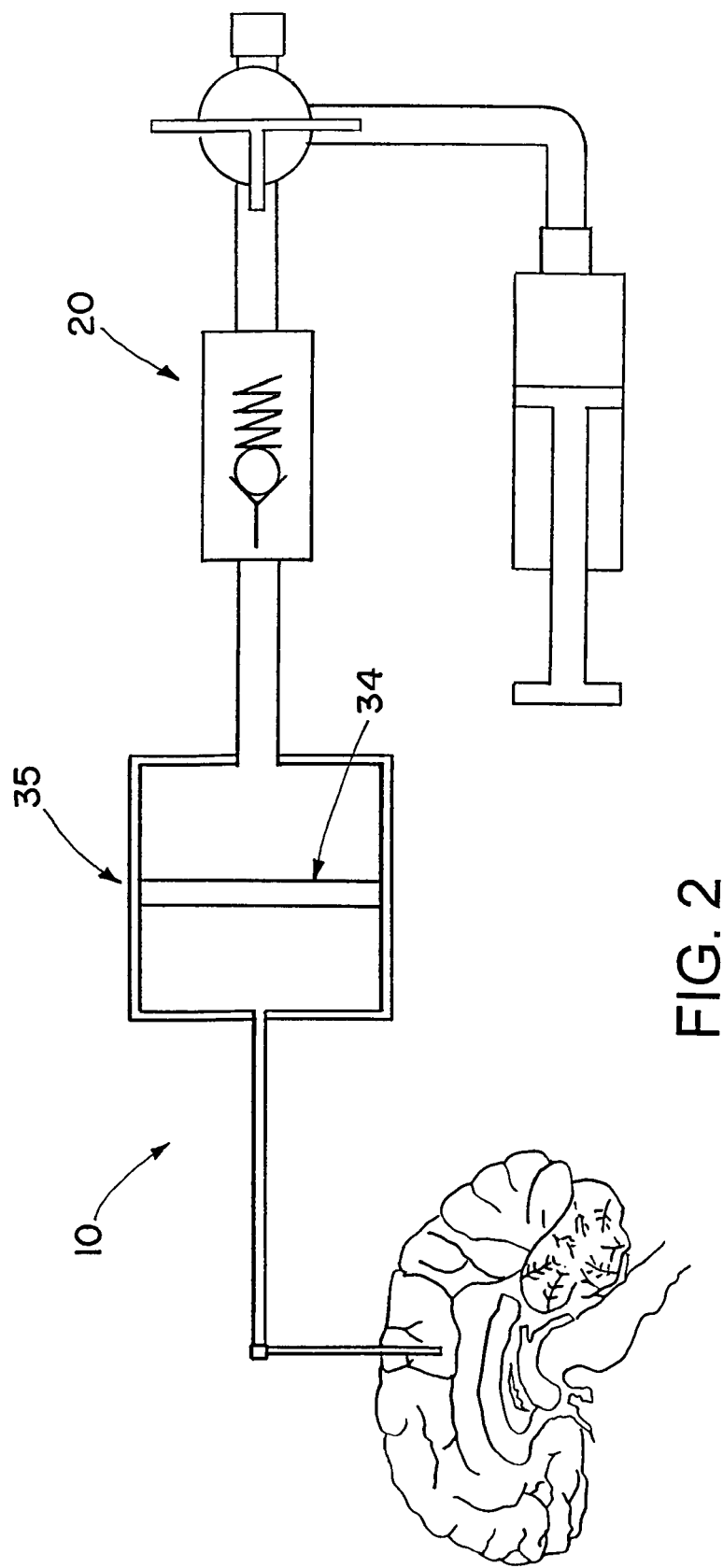
FIG. 2 a system in accordance with the invention, in accordance with a second embodiment.

In the slightly modified embodiment of FIG. 2, the depot 35 is sub-divided by a shifting membrane 31 which separates the drug conducting system 10 and the conveying fluid conveying system 20. The membrane 31 prevents contact between the conveying fluid and the drug. In the drawing, therefore, it does not quite reach up to the drug wall only in order to illustrate that it can be shifted.

Figure 3:
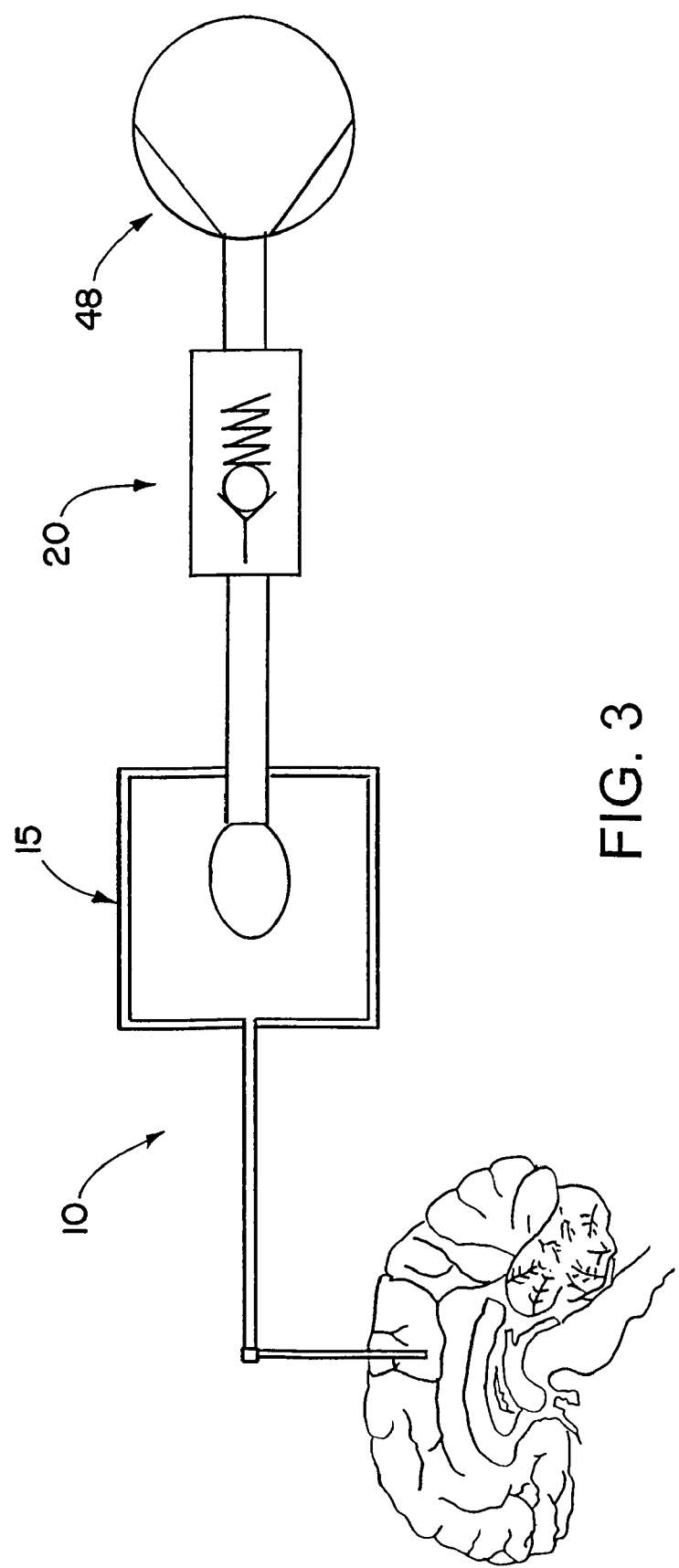
FIG. 3 a system in accordance with the invention, in accordance with a third embodiment.

The conveying fluid pushes the membrane 31 to the left and thus moves the drug to the infusion point. In another embodiment, such as is for example shown in FIG. 3, the syringe or syringe pump can be replaced with any other type of infusion pump, and such an infusion pump is schematically shown in FIG. 3 and provided with the reference sign 48. Pressure-driven pumps can also be used instead of volume pumps, since this has an advantageous effect on the distribution of the drug.

Figure 4:
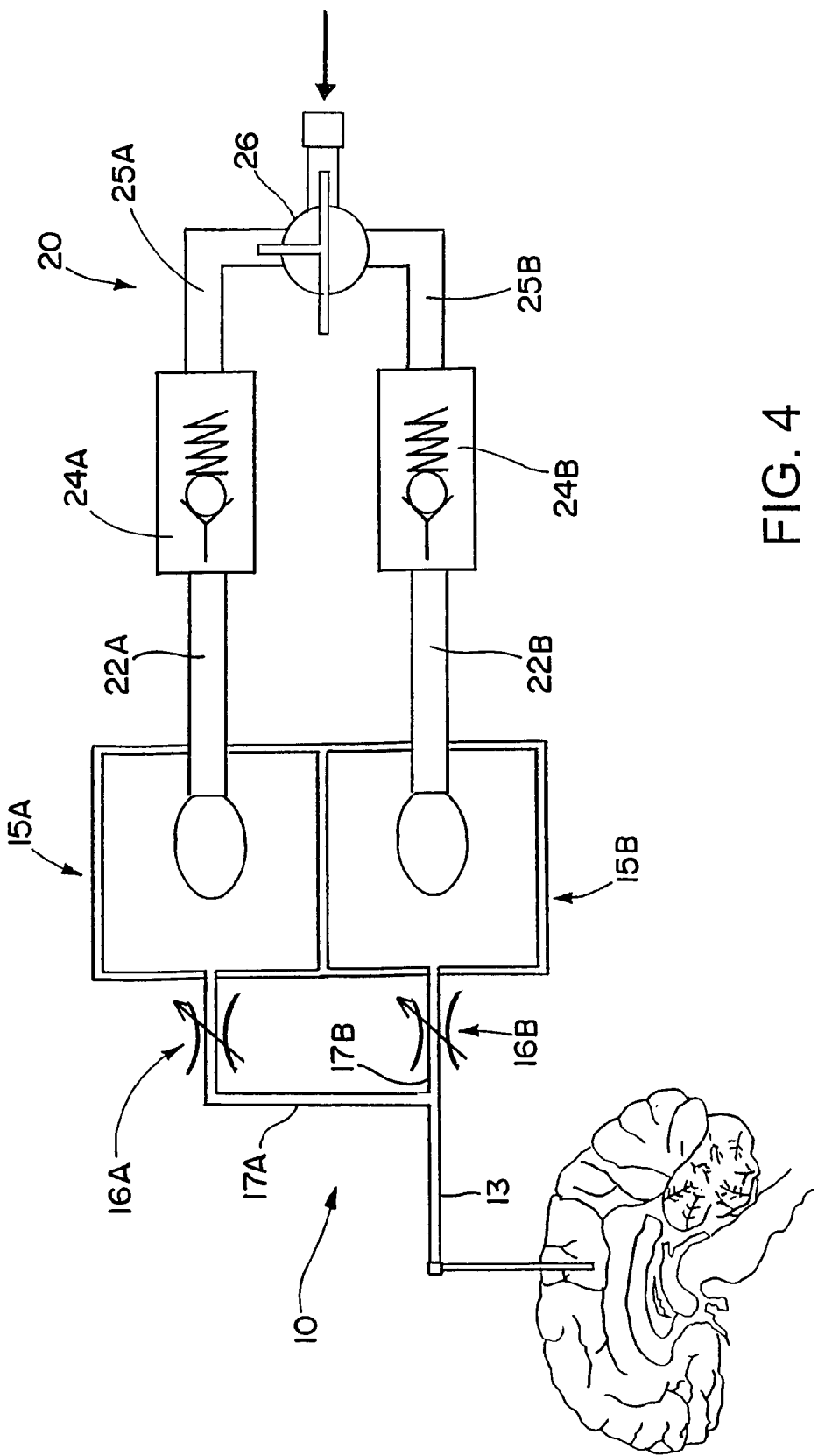
FIG. 4 a system in accordance with the invention, in accordance with a fourth embodiment.

In another embodiment, such as is for example shown in FIG. 4, the drug depot has more than one chamber—in FIG. 4, the two chambers and/or individual depots 15A and 15B. The device then comprises two conveying fluid conveying systems, the elements of which are denoted in accordance with FIG. 1, wherein they respectively bear the designations A and B. The three-way valve 26 allows the individual line portions A, B to be connected, disconnected or switched. Such an embodiment can for example be used when different drugs are to be administered or—in chronic applications—in order to be able to refill one depot while the other continues the infusion.

The drug depot can also provide a specific environment if this is necessary. The drug at the depot can for example be cooled, and in accordance with the invention, it is then no longer necessary to also cool the entire conveying system. The entire system, or the drug supply system only, can be embodied as a subcutaneous (implantable) system.

Throttle valves 16A and 16B can additionally be provided on the drug output lines 17A and 17B, as shown in FIG. 4. The throttle valves 16A and 16B can be controlled using external parameters, in order to adapt administering of the drug to such parameters. The parameters can for example be elapsed time or also the concentration of chemical elements or compounds, which are measured by a sensor.

Separating the system filled with the drug from the system filled with the conveying fluid offers various advantages, which are to be cited here again. It prevents air from being introduced into the drug infusion line. Once the drug system has been pre-filled with the drug (primed) and the air has been completely removed from the drug system, no more additional air is introduced into the system due to lines being separated or attached and/or due to separating or reattaching syringes. Avoiding the penetration of air into the infusion line is highly critical to the treatment outcome, since each air bubble in the infusion line or in the tissue increases the backflow of the drug along the catheter, which leads to leakage and an insufficient treatment of the patient. Additional air also leads to a chaotic distribution of the drug which is unpredictable.

A system which allows the syringe or pump to be separated from the infusion line makes various procedures more secure and more efficient. The option of changing the syringes, for example, allows syringes having a smaller volume to be used, which has a positive effect on the backflow length. The greater the syringe volume, the higher the pressure fluctuations in the infusion line due to the action of the syringe pump.

It also becomes possible to interrupt an infusion, for example if an MR scan has to be taken. In order to perform such a scan, the pumps would have to be MR-compatible, which makes them very expensive to produce, or it is necessary to use a very long extension line, which in turn leads to pressure fluctuations in the infusion line.

Currently, catheters are often pre-filled with a saline solution (primed) and then connected to the syringe which contains the drug. This obviously influences the concentration of the drug, and separating the drug from the conveying solution circumvents this problem.

The risk of infection can be significantly reduced in a closed drug system. The drug depot can also for example be worn on the body (for example, on the belt), and it is then possible to use different extension lines having different lengths (for example, a longer line when the patient wishes to move). Additionally, these extension lines for the conveying fluid can be embodied to be more rigid, since movements of the extension line do not directly result in movements of the catheter tube. Rigid tubes and/or lines have lower pressure fluctuations.

Another advantage is that the volume of unused drug can be significantly reduced, because the long lines are filled with conveying fluid and not with the drug. The drug line can be kept relatively short, such that only a little of the—often very expensive—drug remains in the lines once the infusion has been completed.

Computer program elements of the invention may be embodied in hardware and/or software (including firmware, resident software, micro-code, etc.). The computer program elements of the invention may take the form of a computer program product which may be embodied by a computer-usable or computer-readable storage medium comprising computer-usable or computer-readable program instructions, "code" or a "computer program" embodied in said medium for use by or in connection with the instruction executing system. Within the context of this application, a computer-usable or computer-readable medium may be any medium which can contain, store, communicate, propagate or transport the program for use by or in connection with the instruction executing system, apparatus or device. The computer-usable or computer-readable medium may for example be, but is not limited to, an electronic, magnetic, optical, electromagnetic, infrared or semiconductor system, apparatus, device or medium of propagation such as for example the Internet. The computer-usable or computer-readable medium could even for example be paper or another suitable medium on which the program is printed, since the program could be electronically captured, for example by optically scanning the paper or other suitable medium, and then compiled, interpreted or otherwise processed in a suitable manner. The computer program product and any software and/or hardware described here form the various means for performing the functions of the invention in the example embodiments.

Although the invention has been shown and described with respect to one or more particular preferred embodiments, it is clear that equivalent amendments or modifications will occur to the person skilled in the art when reading and interpreting the text and enclosed drawings of this specification. In particular with regard to the various functions performed by the elements (components, assemblies, devices, compositions, etc.) described above, the terms used to describe such elements (including any reference to a "means") are intended, unless expressly indicated otherwise, to correspond to any element which performs the specified function of the element described, i.e. which is functionally equivalent to it, even if it is not structurally equivalent to the disclosed structure which performs the function in the example embodiment or embodiments illustrated here. Moreover, while a particular feature of the invention may have been described above with respect to only one or some of the embodiments illustrated, such a feature may also be combined with one or more other features of the other embodiments, in any way such as may be desirable or advantageous for any given application of the invention.

What is claimed is:

1. A drug supply system for CED (convection-enhanced delivery) catheter infusions, comprising:
   a drug conducting system configured to provide a fluid seal between a drug to be administered and other fluids of the drug supply system, the drug conducting system including
   i) a drug depot for storing the drug to be administered, and
   ii) a catheter supply line coupled to said drug depot;
   a conveying device configured to convey the drug from the drug depot into the catheter supply line; and
   a conveying fluid conveying system arranged between the conveying device and the drug conducting system, said fluid conveying system connected to the drug depot via a drug displacement element, and connected to the conveying device,
   wherein the conveying fluid conveying system comprises a line system including a three-way distributor and/or a reflux valve arranged in the line system.

2. The drug supply system according to claim 1, wherein the drug displacement element comprises a flexible membrane arranged in or on the drug depot and, when dilated, displaces the drug from the depot into the catheter supply line.

3. The drug supply system according to claim 2, wherein the flexible membrane is an elastic membrane.

4. The drug supply system according to claim 2, wherein the membrane comprises an inflatable device arranged in the drug depot.

5. The drug supply system according to claim 1, wherein the drug displacement element comprises a shifting wall in or on the drug depot, said shifting wall configured to move by contact pressure from the conveying fluid to displace the drug from the depot into the catheter supply line.

6. The drug supply system according to claim 1, wherein the conveying fluid conveying system comprises a line system including a connector configured to releasably couple the conveying device to/from the conveying fluid conveying system and connecting point.

7. The drug supply system according to claim 6, wherein the separating and connecting point is a quick-release connection.

8. The drug supply system according to claim 1, wherein the three-way distributor comprises a three-way stop cock and/or straight-way cock.

9. The drug supply system according to claim 1, wherein the drug depot is sub-divided into a number of chambers or the drug conducting system comprises a plurality of drug depots, wherein each chamber and/or depot comprises an independent conveying fluid supply line.

10. The drug supply system according to claim 9, wherein the conveying fluid supply lines can be switched individually or together and charged with conveying fluid by the conveying fluid conveying device.

11. The drug supply system according to claim 1, wherein the conveying fluid conveying system is a mechanically charged syringe or a pump.

12. The drug supply system according to claim 1, further comprising a drug supply controller and/or regulator configured to control and/or regulate how the drug is administered.

13. The drug supply system according to claim 12, wherein the drug supply controller and/or regulator controls and/or regulates how the drug is administered in accordance with measured external parameters.

14. The drug supply system according to claim 13, wherein the measured external parameters comprise at least one of elapsed time, temperature or particular concentrations of chemical elements and/or compounds.

15. The drug supply system according to claim 1, further comprising the drug displacement element, said drug displacement element comprising at least one of a flexible membrane, a moving wall, or a balloon.

* * * * *